(12) United States Patent
Freund et al.

(10) Patent No.: US 6,843,773 B2
(45) Date of Patent: Jan. 18, 2005

(54) BLOOD PRESSURE MONITORING DEVICE AND METHOD OF MANUFACTURING A PARTS MOUNTING MODULE OF A BLOOD PRESSURE MONITORING DEVICE

(75) Inventors: Dirk Freund, Kelkheim (DE); Martin Giersiepen, Oberursel (DE); Brigitte Harttmann, Niedernhausen (DE); Ulrich Heck, Krefeld (DE); Stefan Hollinger, Kronberg (DE); Frank Kressmann, Schwalbach (DE); Gerrit Rönneberg, Darmstadt (DE); Fred Schnak, Kronberg (DE); Christoph Rennefeld, Königstein (DE); Rainer Hans, Waldems (DE)

(73) Assignee: Braun GmbH, Kronberg ( * ) Notice: Subject to any disclaimer, the term of this patent is extended or adjusted under 35 U.S.C. 154(b) by 135 days.

(21) Appl. No.: 10/167,838

(22) Filed: Jun. 12, 2002

(65) Prior Publication Data

US 2002/0156382 A1 Oct. 24, 2002

Related U.S. Application Data

(63) Continuation of application No. PCT/EP00/13093, filed on Dec. 21, 2000.

(30) Foreign Application Priority Data

Dec. 29, 1999 (DE) .......................................... 199 63 623

(51) Int. Cl.$^7$ ................................................ A61B 5/02
(52) U.S. Cl. ...................................................... 600/490
(58) Field of Search ........................ 600/490, 492–496, 600/498, 499, 500–503, 481, 485

(56) References Cited

U.S. PATENT DOCUMENTS

| 3,118,440 A | | 1/1964 | De Dobbeleer |
| 5,220,925 A | * | 6/1993 | Hishida ....................... 600/493 |
| 5,464,019 A | * | 11/1995 | Anderson et al. ........... 600/490 |
| 5,692,512 A | * | 12/1997 | Flachslaender ............. 600/490 |
| 6,251,080 B1 | * | 6/2001 | Henkin et al. ............... 600/490 |

FOREIGN PATENT DOCUMENTS

EP      0 769 266 A1    4/1997

OTHER PUBLICATIONS

Findeisen, H., Gas geben und Kosten sparen in Z: Kunststoff–Journal, Sep. 1995, S.37 bis 40.

* cited by examiner

Primary Examiner—Robert L. Nasser
Assistant Examiner—Navin Natnithithadha
(74) Attorney, Agent, or Firm—Fish & Richardson P.C.

(57) ABSTRACT

The invention is directed to a blood pressure monitoring device comprising a central parts mounting module and to a method of manufacturing this parts mounting module. According to the invention fluid channels are produced by gas injection into the interior of the parts mounting module, the walls bounding the fluid channels being completely formed by the material of the parts mounting module. The injection of gas continues for as long as a core of the parts mounting module is still in the liquid phase in the area of the fluid channel, whilst an outer area surrounding the core has already solidified, so that the pressure fluid expels the liquid core area, producing a tubular fluid channel.

24 Claims, 8 Drawing Sheets

BLOOD PRESSURE MONITORING DEVICE AND METHOD OF MANUFACTURING A PARTS MOUNTING MODULE OF A BLOOD PRESSURE MONITORING DEVICE

CROSS-REFERENCE TO RELATED APPLICATIONS

This application is a continuation of PCT application number PCT/EP00/13093 filed on Dec. 21, 2000, and claims priority from German application serial number 19963623.0 filed on Dec. 29, 1999.

FIELD OF THE INVENTION

This invention relates to a blood pressure monitoring device with a fluid pressure system for filling a cuff with fluid under pressure and with a parts mounting module having bays for receiving components of the fluid pressure system, provision being made for at least one fluid channel integrated in the mounting module and serving the function of connecting the components.

The present invention further relates to a method of manufacturing such a parts mounting module with a fluid channel extending in the interior thereof. Furthermore, the invention relates to a die for implementing the method.

BACKGROUND OF THE INVENTION

It is conventional practice to apply the cuff of a blood pressure monitoring device to a subject's limb, in particular to his or her upper arm or wrist, and inflate it until arterial occlusion sets in. The fluid pressure system provided for this purpose typically comprises a pump for cuff inflation, a valve for discharge of the pressure fluid, and a pressure sensor for detecting the cuff pressure from whose fluctuations caused by the blood pressure during the inflation and deflation cycles the blood pressure is then determinable by means of an evaluating unit.

For connecting the components of the fluid pressure system it is known to use a rubber tubing having arranged around it all the components exposed to pressure, in which arrangement however both the assembly and the design freedom of the individual components are subject to restrictions. The fluid channels may be formed by tubing or molded parts coupled together internally. An automated assembly of this "internal tubing" is practically not possible because of the soft material properties and the small dimensions of the tubes.

From EP 0 769 266 A1 a blood pressure monitoring device is known in which the fluid channels are integrally formed in a mounting module for the components of the fluid pressure system. In this device, the injection-molded mounting module has on its upper side recesses in the form of grooves which are closed and sealed with a film material adhesive-bonded to the upper side so that fluid channels are produced. For the film to adhere it is however necessary for the upper side to be plane or to have no more than a one-dimensional curvature, which imposes limitations on the freedom of design and relative arrangement of the individual components. In addition, the film is relatively sensitive and hence subject to increased wear. Furthermore, the film is extensible to a considerable degree which may result in a pressure pulse characteristic developing in the fluid channel which produces a measurement error. Finally, contact with the cover film entails the risk of pressure surges occurring in the fluid channel, hence introducing measurement errors. For a fluid-tight configuration of the connection between film and upper side a coating of hot-melt adhesive was used which requires an appropriate temperature treatment.

It is therefore an object of the present invention to provide an improved blood pressure monitoring device of the type initially referred to, an improved method of manufacturing the parts mounting module of the blood pressure monitoring device, and a die for implementing said method, which avoid the known shortcomings of the prior art. The aim is in particular to provide an improved mounting module for the components of the fluid pressure system, which affords ease of assembly of the blood pressure monitoring device and contributes to a compact design of the blood pressure monitoring device.

BRIEF SUMMARY OF THE INVENTION

With regard to the blood pressure monitoring device the foregoing object is accomplished in a blood pressure monitoring device of the type initially referred to in that the wall bounding the fluid channel is integrally formed of one piece completely by the material of the parts mounting module.

The wall of the fluid channel consists exclusively of the material of the parts mounting module. The fluid channel wall is not made up of sections made of film, covers or the like with which an open fluid channel in the mounting module would have to be closed in the first place. In cross section the channel is completely covered by the module material.

This simplifies manufacture in so far as it obviates the step of adhesive-bonding a film to the upper side of the parts mounting module. The arrangement of the fluid channel completely in the interior of the module material increases the resistance of the fluid channel walls to pressure. The known pressure pulse characteristic is thus prevented from developing, and the accuracy of measurement is enhanced. Furthermore, the routing of the fluid channel can be designed without having to make allowance for the film to be adhered. There is no need for the fluid channel to extend along an upper side which has to be plane or allows only a one-dimensional curvature to ensure adhesion of the film. Rather, the fluid channel may be routed freely, resulting in a great freedom of design with respect to the arrangement of the components of the fluid pressure system. This enables the blood pressure monitoring device to be built to compact dimensions.

In particular, the fluid channel may be routed in a three-dimensional curvature extending in several planes. This results in maximum design freedom as regards the arrangement of the components of the blood pressure monitoring device.

It will be appreciated that the parts mounting module of the blood pressure monitoring device may be made of a variety of materials. Equally, the fluid channel may be produced in a variety of ways. According to a preferred embodiment of the invention, the parts mounting module is injection molded from a preferably thermoplastic material, in particular from ABS.

In a further aspect of the invention, the fluid channel divides into several fluid channels in the interior of the material of the parts mounting module. The fluid channel hence possesses plural interconnected branches. This enables a plurality of components of the fluid pressure system to be interconnected, in particular an additional branch of the fluid channel may be provided to connect a deflation valve with the fluid channel for deflating the cuff.

Advantageously, the components of the fluid pressure system are connected to the fluid channel directly. The need to provide connecting lines and the like is obviated. For this purpose, the fluid channel is provided with ports into which the corresponding component can be snap-fitted with an essentially complementary connector element. The connection may also be established vice-versa, meaning that the port is provided in the corresponding component while the mounting module has at the end of the fluid channel a connector element adapted to be snapped into the port. All that is required for assembly is to snap the components of the fluid pressure system into or onto the parts mounting module, which results in considerable assembly cost savings. To effect a tight seal of the connection between the components and the fluid channel the design of the port is of importance. It will be understood that a variety of designs are possible in this context. Both axial and radial seals are feasible, with the fluid channel requiring an outlet underneath the axial sealing area. In particular each port may possess a cylindrical section. The use of an O-ring is sufficient to effect a seal.

According to another aspect of the present invention, all the remaining components (including, for example, deflation valve, pump, pressure sensor, inclination sensor, electronic components, printed circuit board, power source and cuff) of the blood pressure monitoring device are mounted on the mounting module. Hence the parts mounting module is the central part on which the other components are mountable directly. Particularly the cuff of the blood pressure monitoring device may be snapped onto the mounting module directly, thereby eliminating the need to provide tubing for inflating the cuff and enabling the blood pressure monitoring device to be built to highly compact overall dimensions. It is also possible to mount on the central parts mounting module a control unit for evaluation of the measurement values and determination of the blood pressure and the contacts of a power source for operating the evaluating or control unit. Mounting all the components of the blood pressure monitoring device on the mounting module has the advantage that the blood pressure monitoring device builds to compact dimensions, irrespective of the previously described special configuration of the fluid channel or its wall.

Plural advantages are attendant upon the fact that the components of the blood pressure monitoring device such as the pump, the printed circuit board, the cuff, the pressure valve, the pressure sensor, the deflation valve where applicable, the power source, etc. are not received in recesses specifically formed in the housing for this purpose, provision being made instead for a parts mounting module formed (and manufactured) separate from the housing, which receives all the components. For one purpose, this modular design allows great freedom regarding the shape design of the housing because otherwise the component geometry would dictate the shape design of the housing to a certain extent. For another purpose, the arrangement of the components of the blood pressure monitoring device in bays in the mounting module or a chassis part ensures great ease of assembly of the blood pressure monitoring device. The quality assurance test of all the functional parts is performed on the fully packed mounting module without the housing, which eliminates the need to protect a housing from being marred during the test cycle, in addition to providing for ready accessibility of all the components. Furthermore, this modular design employing a parts mounting module or chassis in which all the components are received is also highly impact resistant.

According to a preferred embodiment of the invention, the cuff is arranged on an underside while the components of the fluid pressure system, particularly its pump, pressure valve and pressure sensor are arranged on an upper side of the parts mounting module and coupled to fluid channel ports. This produces particularly short fluid connections between the components of the fluid pressure system and with the cuff. Furthermore, the mounting module may be constructed as a molded shell for the cuff, enabling it to be conformed to the arm or the wrist.

To obtain a particularly compact blood pressure monitoring device the components of the fluid pressure system having an electrical connection, in particular the pump, the pressure valve and the pressure sensor, are advantageously arranged such that their electrical connections lie essentially in one plane. The electrical components may be connected to a printed circuit board directly and, via this board, to a corresponding control unit. It is thus possible for the electric control and supply to be free from wiring. This facilitates the assembly significantly. The components of the blood pressure monitoring device equipped with electrical connections are all arranged on the one side of the mounting module, so that the contacts are located approximately in one plane, permitting direct connection or soldering to the printed circuit board. Mounted on the printed circuit board are also all the typical electrical components including, for example, resistors, capacitors, ASICs, MPU or control unit and programmable controller, in order to control all the components of the blood pressure monitoring device in accordance with the oscillometric method.

With regard to the method, the object referred to in the foregoing is accomplished according to the invention by a method of manufacturing the parts mounting module with a fluid channel extending in the interior thereof, which includes the steps of bringing the parts mounting module in at least one region of the fluid channel to be produced therein in a condition in which a core area is in the liquid phase while an outer area surrounding it is in the solid phase, and pressurizing the liquid core area with a pressure fluid, in particular gas, and expelling it out of the parts mounting module so that a tubular fluid channel is produced. The method of manufacturing such channels in plastics materials is known as gas-assist injection molding.

In this method, a different temperature distribution is generated in the parts mounting module, to the effect that the temperature in the core area corresponds to or exceeds the liquidus temperature of the material, while the temperature in the outer area is maintained below the liquidus temperature. A jet of gas blows or flushes the liquid core out, producing a fluid channel lying completely in the interior of the material.

The method of the invention is not only suitable for utilization in connection with the manufacture of a parts mounting module of a blood pressure monitoring device but may be used generally for the manufacture of components for products for personal use, in order to provide function channels, in particular pressure channels. In this context, particular advantages result with respect to said parts mounting module of a blood pressure monitoring device.

In a further aspect of the invention, the parts mounting module is injection-molded from a plastics material, and pressurization with compressed gas takes place once the outer area has solidified while the core area is still in the liquid phase. Compressed gas is applied shortly after injection of the plastics material. This period of time may depend on various parameters such as the material employed. In cases where a thermoplastic material is used, the pressure channel is blown out after a period of about one tenth of a second up to some seconds has elapsed. The outer area of the mounting module solidifies relatively rapidly due to its contact with the injection mold. The temperature of the mounting module, particularly its core area, generally lies in the range of the melting point of the material.

According to a preferred embodiment of the invention, the fluid channel has a wall of an essentially uniform, in particular roughly constant thickness in cross section. It will be understood, of course, that this may not apply to the ends or port areas of the fluid channel. During the injection and cooling cycles of the mounting module the uniform wall thickness ensures that the material solidifies evenly from the outside towards the core, so that a substantially central and rectilinear fluid channel is obtained by blowing out the still liquid core.

As pressure fluid a gas, particularly nitrogen, may be used for blowing out the liquid core in the fluid channel. The use of a liquid such as water is equally possible.

In another aspect of the invention the gas is introduced into the parts mounting module at a pressure in the region of several 100 bar, in particular 40 to 500 bar, preferably 100 to 350 bar. With pressures of this magnitude high-precision fluid channels are achieved. The requisite pressure depends, for example, on the length of the fluid channel, the viscosity of the material and other parameters.

According to an advantageous embodiment of the invention, a bifurcating fluid channel may be provided in the parts mounting module. Preferably, a first step includes forming the fluid channel along the one branch, and a second step includes forming the other branch. Conveniently, the first step further includes opening the outlet of the fluid channel of the one branch while closing the outlet of the fluid channel of the other branch and introducing the pressure fluid into the fluid channel from the upstream side of the bifurcation. The second step further includes closing the outlet of the fluid channel of the one branch while opening the outlet of the fluid channel of the other branch, so that the fluid channel can be blown out along the other branch.

According to a further aspect of the present invention, a die is provided for implementing the method with an injection mold and a pressure fluid device for introducing pressure fluid into the interior of the injection mold, said die being characterized according to the invention in that the injection mold has at the mouth of the fluid channel a closable and re-openable discharge opening for ejection of the liquid core material.

With the discharge openings initially closed, the plastics material is injected into the mold, initially filling completely in the injection die the pressure fluid channels to be produced. In the second step the filled fluid channels are blown out by the injected gas. As this occurs, the discharge opening in the die is opened. The entering gas volume forces the still liquid plastic melt out of the discharge openings until the gas stream exits the mouth of the channel.

The injection mold may be provided with several such discharge openings.

These and further features will become apparent not only from the claims but also from the description and the accompanying drawings, and it will be understood that the individual features, whether taken alone or combined in the form of sub-combinations, may be implemented in an embodiment of the invention and in other fields including, for example, other products for personal use, and represent advantageous embodiments.

BRIEF DESCRIPTION OF THE DRAWINGS

An embodiment of the present invention is illustrated in the accompanying drawings and will be explained in greater detail in the following. In the drawings.

DETAILED DESCRIPTION

Figure 1:
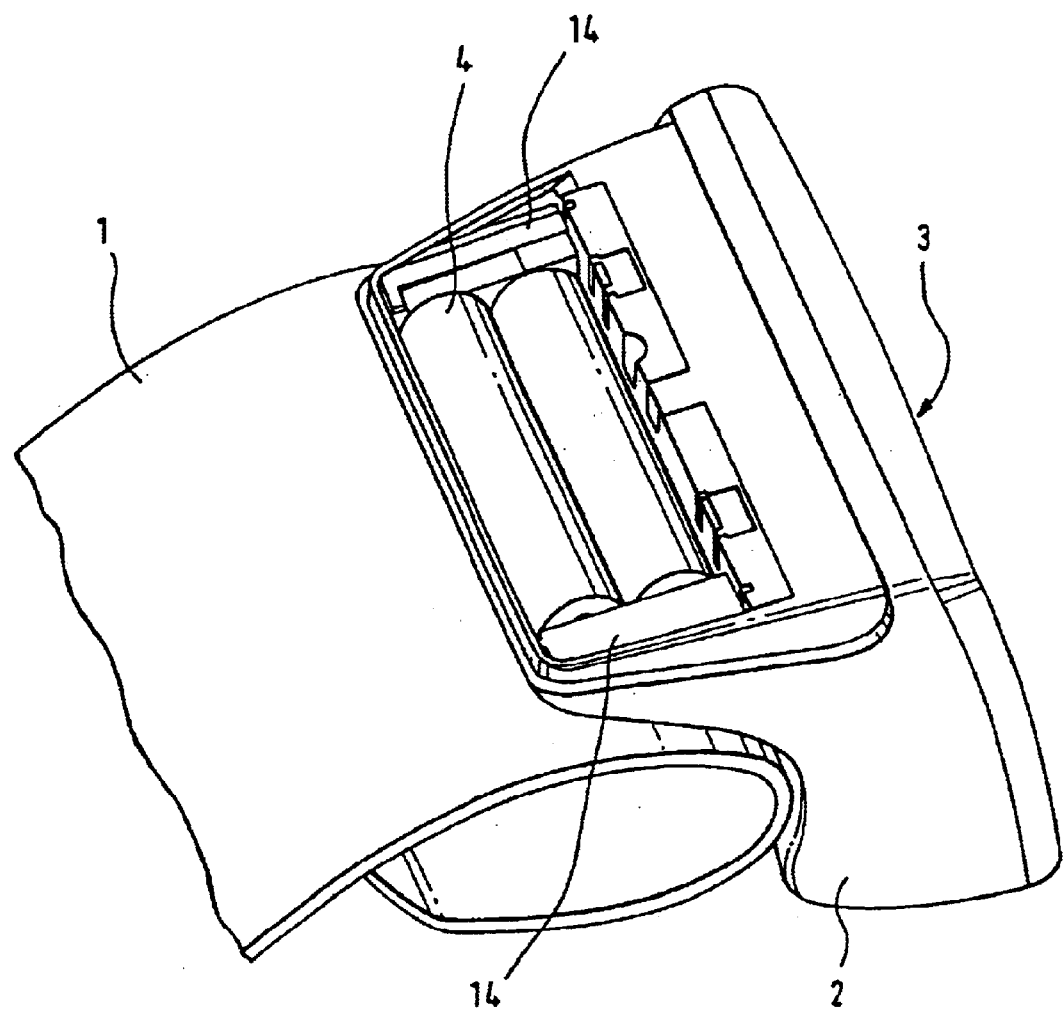
FIG. 1 is a perspective view of a blood pressure monitoring device comprising a cuff and a function housing receiving therein the fluid pressure system and an evaluating unit for evaluating the blood pressure, visible only by the battery contact area.

FIG. 1 shows a blood pressure monitoring device comprising a cuff 1 inflatable with air. The cuff 1 can be wrapped around a subject's arm or wrist for occluding a blood vessel by inflation—as is conventional practice in the oscillometric method of measuring blood pressure. As shown in FIG. 1, the blood pressure monitoring device further comprises a housing 2 which on its side adjoining the cuff is shaped to conform to the arm contour. Arranged on the side facing away from the cuff is a display device 3 for indicating the measured blood pressure (systolic, diastolic and pulse). The housing 2 has a cover shown removed in FIG. 1 to insert batteries 4 for power supply of the blood pressure monitoring device. In the interior of the housing 2 is a central parts mounting module 5 which will be described in greater detail subsequently.

Figure 2:
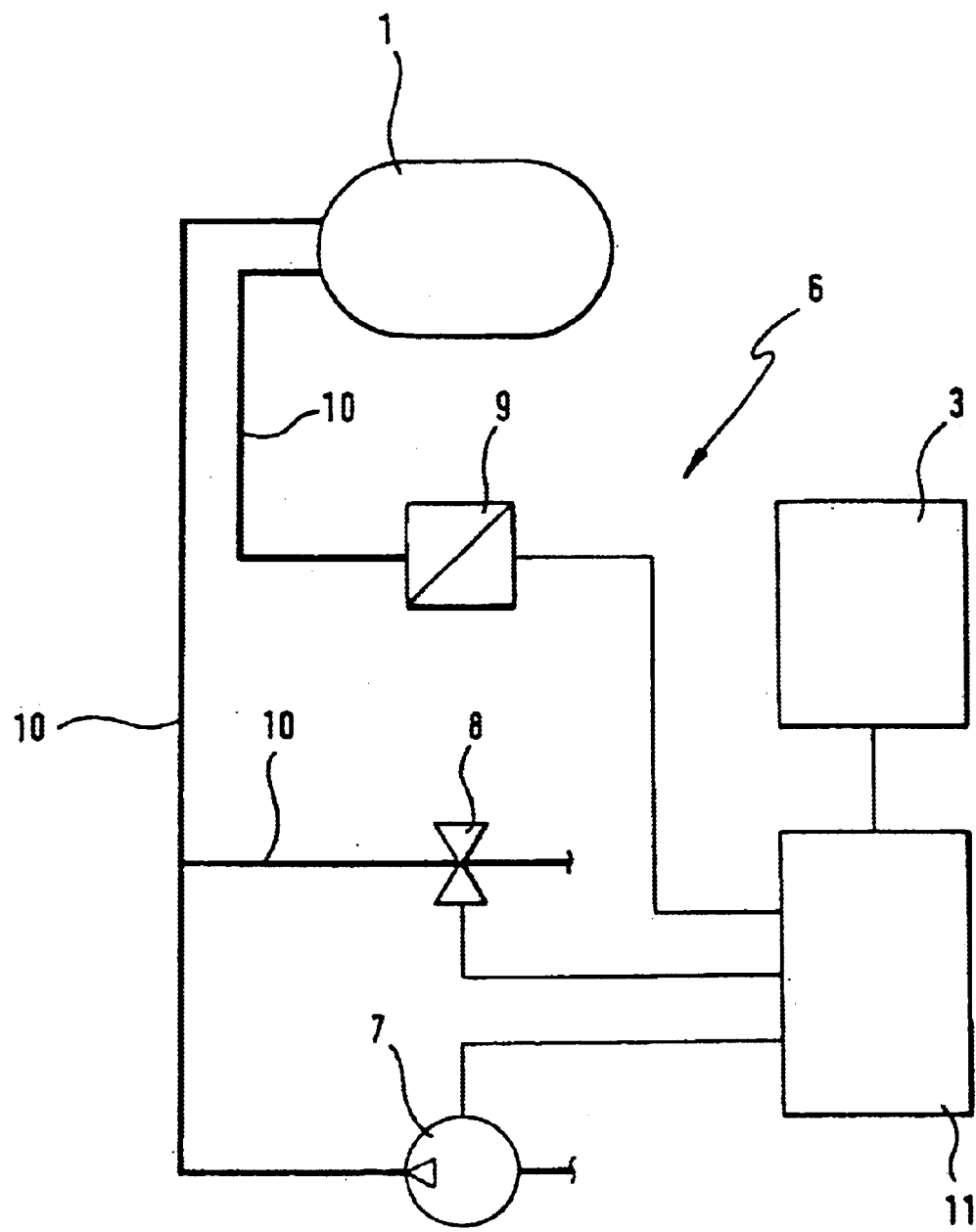
FIG. 2 is a schematic circuit diagram of the components of the fluid pressure system and the evaluating unit.

The blood pressure monitoring device is equipped with a fluid pressure system 6 for inflating the cuff 1. As FIG. 2 shows, the fluid pressure system 6 comprises a pump 7, a valve 8 and a pressure sensor 9 which are each in fluid communication with the cuff 1 through fluid channels 10. The components of the fluid pressure system 6 operate electrically, being each connected with a control unit 11 configured as a controller. There is no wiring provided for connection, instead all the electrical parts are directly soldered to a card or printed circuit board as will be described in more detail later. The fluid channels 10 are integrally formed in the central parts mounting module 5.

Figure 4:
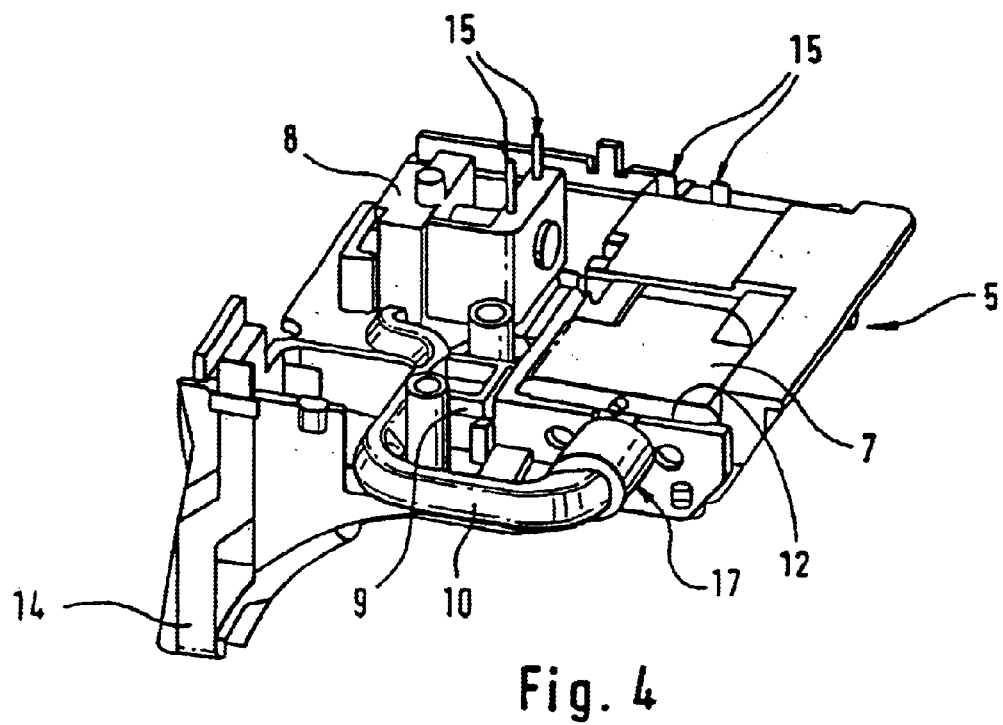
FIG. 4 is a perspective view of the parts mounting module similar to FIG. 3 but showing the mounting module from above.

The parts mounting module 5 is injection molded from ABS. All the components of the blood pressure monitoring device are mounted on the central mounting module 5. As FIG. 4 shows, the pump 7 is inserted in a suitable bay 12 (shown on FIG. 5) in the mounting module 5, the valve 8 is received in a corresponding recess, and the pressure sensor 9 in an appropriate recess of the mounting module (cf. FIG. 4).

Figure 3:
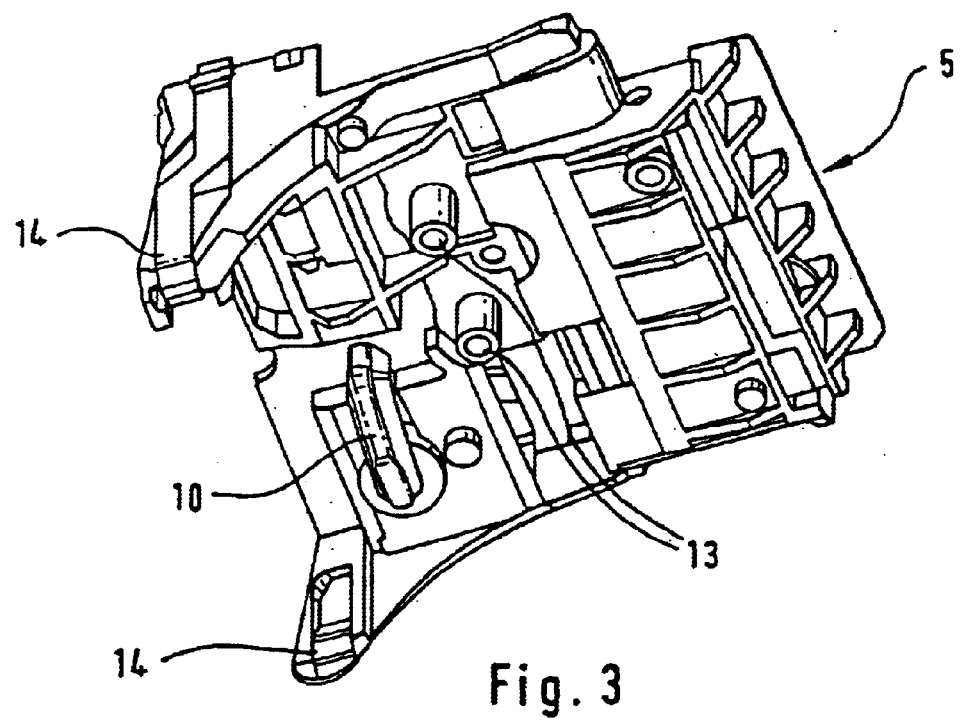
FIG. 3 is a perspective view, from below, of a preferred embodiment of a parts mounting module of the blood pressure monitoring device.

On the opposite side of the mounting module 5 provision is made for two connector necks 13 (cf. FIG. 3) for attachment and connection of the cuff 1. Integrally formed on the mounting module 5 are two support arms 14 receiving between them the batteries 4. With two ribs shaped to conform to the arm contour the two support arms 14 take support upon the main body of the mounting module 5 (cf. FIGS. 1, 3 and 4).

Figure 11:
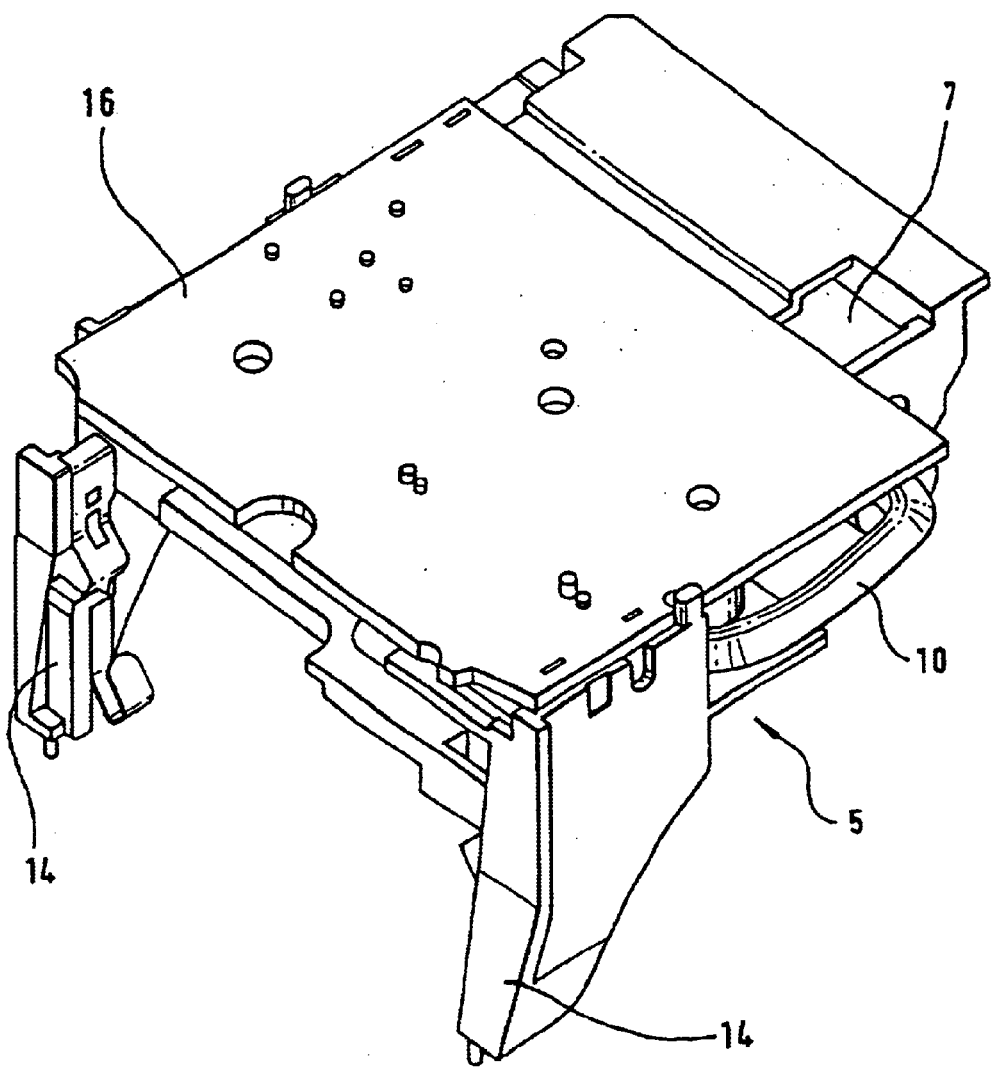
FIG. 11 is a perspective view of the parts mounting module as seen looking from an upper side, illustrating a printed circuit board mounted on said upper side.

The electrical components of the fluid pressure system 6, that is, the pump 7, the valve 8 and the pressure sensor 9, are all arranged on the same side of the mounting module 5. The arrangement of the components is such that their contacts 15 lie approximately in one plane (cf. FIG. 4), which enables them to be easily soldered to a printed circuit board 16 (cf. FIG. 11). This results in a compact design and renders wiring unnecessary. The control unit with the controller and the electronic components is provided on the printed circuit board 16 which is equally mounted on the mounting module 5. The side of the printed circuit board 16 facing away from the mounting module is fixedly connected with the display device 3. As an option it is also possible to accommodate an inclination angle sensor in a suitable further recess in the mounting module 5 in order to determine the spatial position of the blood pressure monitoring device. The parts of the housing 2 illustrated in FIG. 1 are equally fixedly mounted on the mounting module 5. Hence all the constituent parts of the blood pressure monitoring device are secured to the mounting module 5. Following a manufacturing and assembly process, this makes it possible, for example, to perform a test for proper functioning on the mounting module as a unit on which all the system components are readily accessible, excluding perhaps the cuff and the housing parts, hence eliminating the need to perform individual function tests on individual units successively.

The components of the fluid pressure system 6 are interconnected by fluid channels formed in the parts mounting module 5. The fluid channels 10 extend along a three-dimensional curved path in several planes (cf. FIGS. 4, 5, 6 and 10) for maximum space economy and compact arrangement of the components of the fluid pressure system 6 while at the same time ensuring their connection with the cuff 1. The fluid channel 10 leading away from the pump 7 bifurcates into two fluid channels, one being routed to the cuff 1 and the other to the valve 8 (cf. FIG. 5). As the Figures show, the fluid channels 10 are formed in the manner of a bead as a projection raised relative to the balance of the mounting module material, so that the walls of the fluid channels 10 are of a substantially uniform, in particular roughly constant thickness and the cooling cycle proceeds evenly during the injection molding operation.

Figure 7:
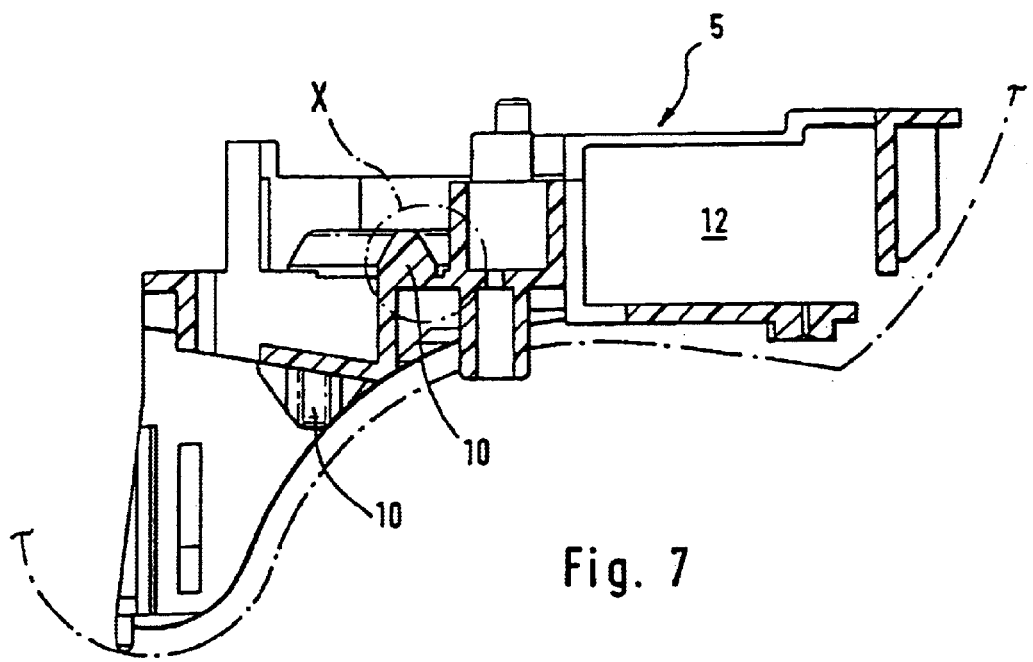
FIG. 7 is a sectional view of the parts mounting module taken along the line I—I of FIG. 5.
Figure 8:
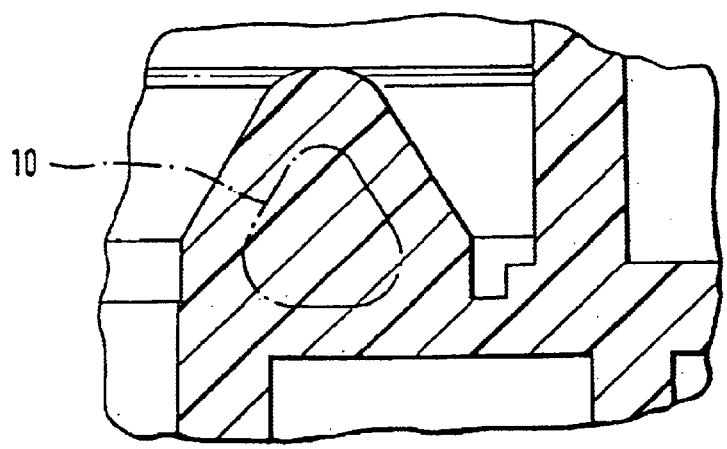
FIG. 8 is a sectional view, on an enlarged scale, of a fluid channel in an area marked X in FIG. 7, said fluid channel being shown prior to being blown out.

FIGS. 7 and 8 show a fluid channel 10 in cross section as it presents itself immediately following injection molding of the mounting module 5, meaning that the entire channel is still filled with the plastics material of the mounting module 5, being not blown out as yet. The dot-and-dash line in FIG. 8 shows the substantially uniform wall thickness of the fluid channel 10.

The parts mounting module 5 is produced with the aid of the gas-assist injection molding technique, in which excess plastics melt is expelled out into a secondary cavity whose volume is adapted to the displaced volume, as follows:

First, liquid plastics material is injected into an injection mold shaped to conform to the mounting module 5, in which process also the fluid channels 10 are completely filled with the injection molding material. The injected plastics material initially cools off along the mold walls so that the outer areas of the mounting module 5 more proximate to the surface are the first to solidify while the core areas of the mounting module 5 are still liquid. This applies in particular to the thick-walled plastics profiles in which a fluid channel 10 is to be provided subsequently.

The injection mold has opposite the fluid channel 10 a discharge opening closable and openable again by a slide or the like. Provided at the opposite end of the fluid channel is a pressure fluid device by means of which a pressure fluid, particularly nitrogen, may be injected into the injection mold at the appropriate location. The gas injection nozzle is applied to the selected site of the pump port 17. Shortly after the plastics material is injected into the mold, after about one tenth of a second up to some seconds following injection, the discharge opening, which was closed during injection molding, is opened. At the other end of the fluid channel nitrogen is then injected at high pressure, the gas pressure being above the inner pressure of the plastics in the injection mold. The entering gas volume displaces in the core the still liquid plastics melt, expelling it through the discharge openings until the gas stream itself exits the end of the channel.

With gas-assist injection a fluid channel is produced which has no sharp-edged kinks so that favorable flow conditions are achievable.

Figure 5:
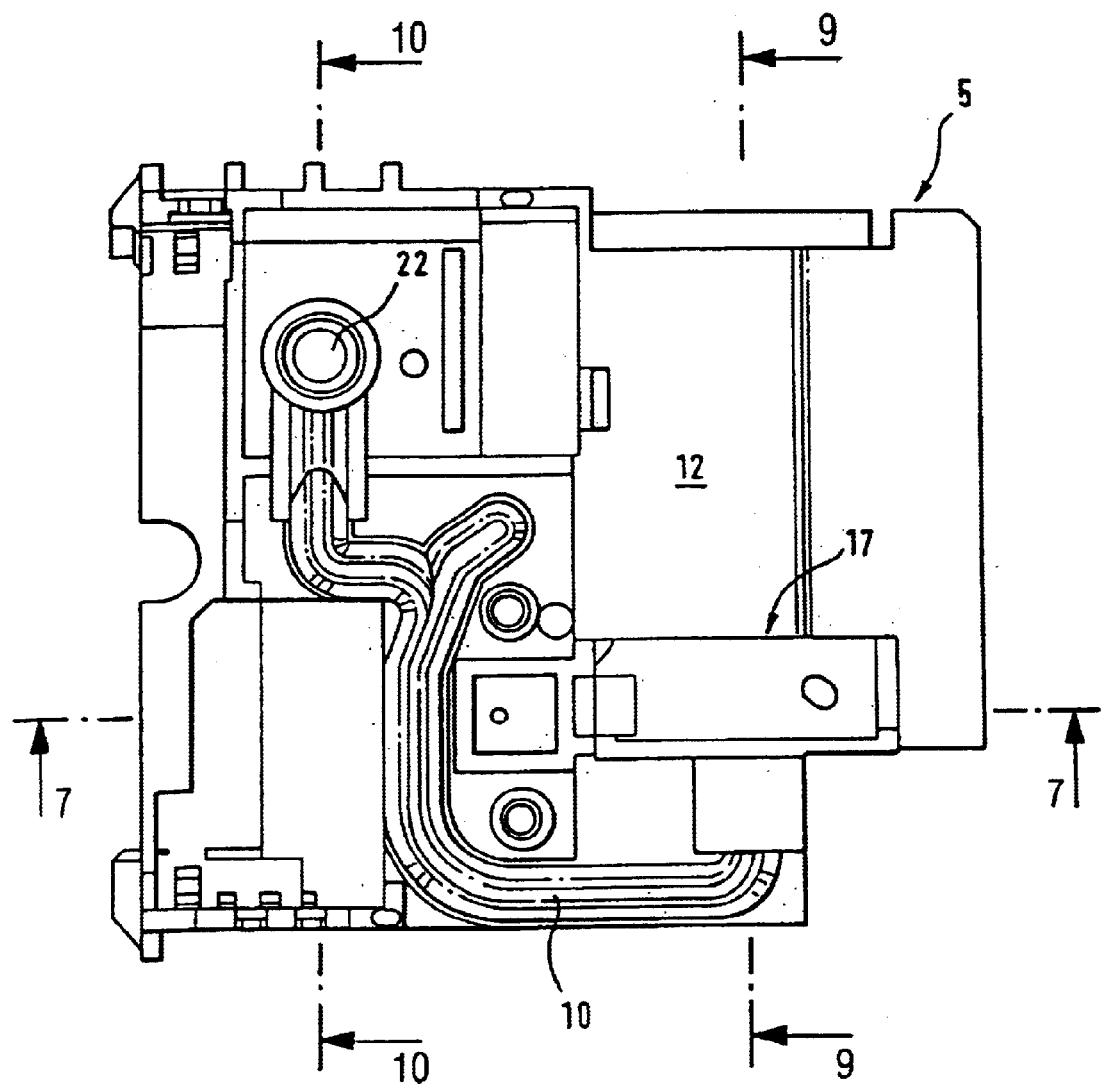
FIG. 5 is a plan view of the upper side of the parts mounting module illustrating the path of a fluid channel.
Figure 6:
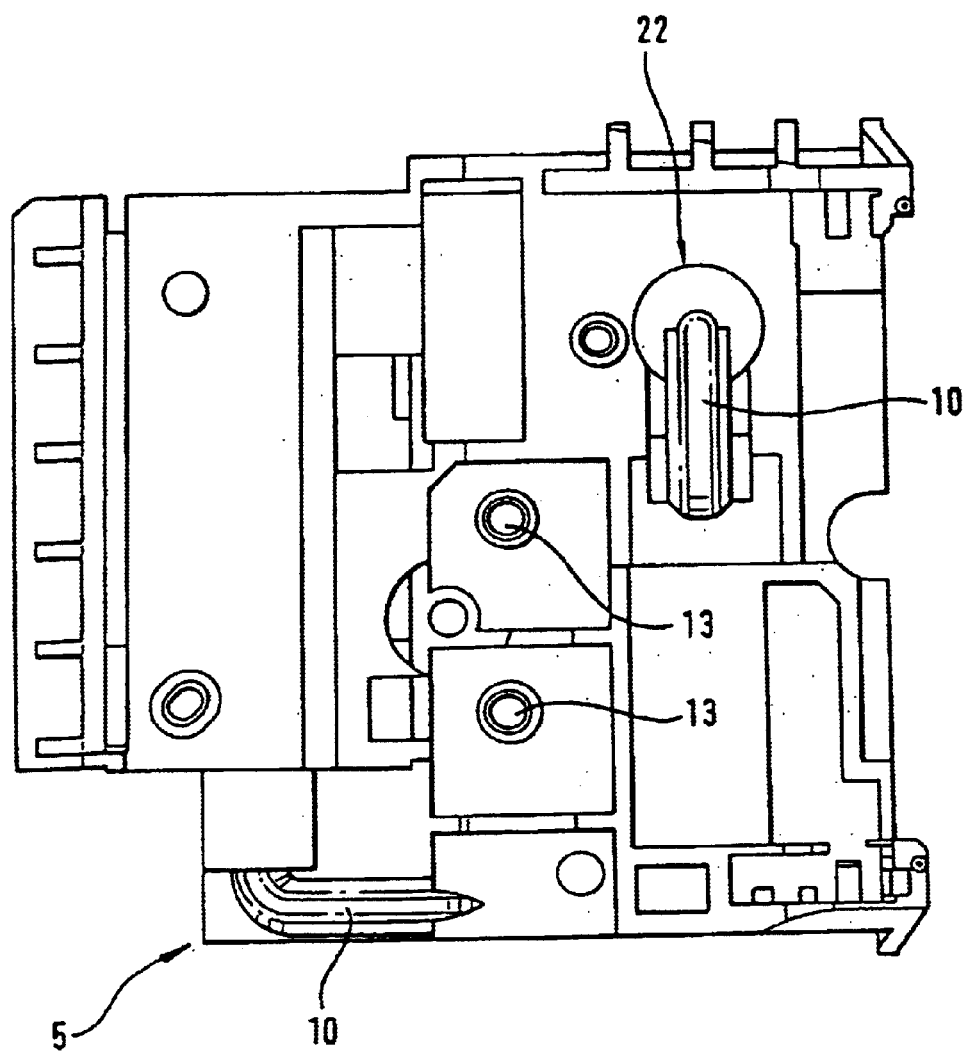
FIG. 6 is a plan view of the lower side of the parts mounting module.

In order to produce the bifurcation in the fluid channel 10 shown in FIG. 5, first a discharge opening in the injection mold at the end of the fluid channel, for example, at the valve 8, is opened while the second end of the fluid channel, for example, at the connector neck 13 for the cuff 1, is maintained closed. As a result, only one branch of the fluid channel 10, that is, the one leading to the valve, is blown out first. The expelled plastics material enters one of the secondary cavities which is of such small dimensions that the pressure in the gas area rises again after a small amount of gas flows in. In a second step the discharge opening at the connector neck 13 is opened, causing the injected nitrogen to force the still liquid core material in the second arm in the direction of the connector neck 13. In this way a T-shaped connecting channel is obtained between the pump 7, the valve 8 and the cuff 1 of the blood pressure monitoring device.

For roundness of the connector necks 13 and the valve port 22 on the other side of the parts mounting module 5 it is important that the injection dies, which are in side-by-side arrangement, be vertically parted in respect of these openings. This means that the direction of movement of the dies proceeds vertically to the axis of the necks 13 and the port 22. With the die parted horizontally relative to the ports 13 and 22, it could happen that the ports 13 and 22 are formed of two semi-circles in offset relation to each other, making it practically impossible, for lack of roundness, to establish a tightly sealed connection between the cuff and the connector necks 13, for example. Roundness of the pump port 17 is ensured by application of the round gas injection nozzle to this opening and the absence of a vertical die parting line extending through the pump port parallel thereto.

The fluid channels 10 lying completely in the interior of the material of the parts mounting module 5 may also be produced with an alternative manufacturing method. In this method the fluid channels 10 could be produced in conventional manner by cores and pushers inserted in the injection die. With this technique, however, exit openings for the die pins would be produced at the end of each channel, which would have to be closed in a separate operation. In addition, only rectilinear channels can be produced, so that a channel following a three-dimensional course would require several such straight-line channel sections which would have to be combined to form the actual fluid channel. In this event several exit openings would have to be closed. The advantages of the previously described gas-assist injection molding method over this method are obvious.

As an alternative to the gas-assist injection molding technique, it is also possible to produce the fluid channels by inserting a prefabricated core system into the plastic mold prior to injection molding the plastic material around it.

The components of the fluid pressure system 6 may be connected to the ports of the fluid channels 10 directly, in particular by a snap action, so that no further fluid lines are necessary.

Figure 9:
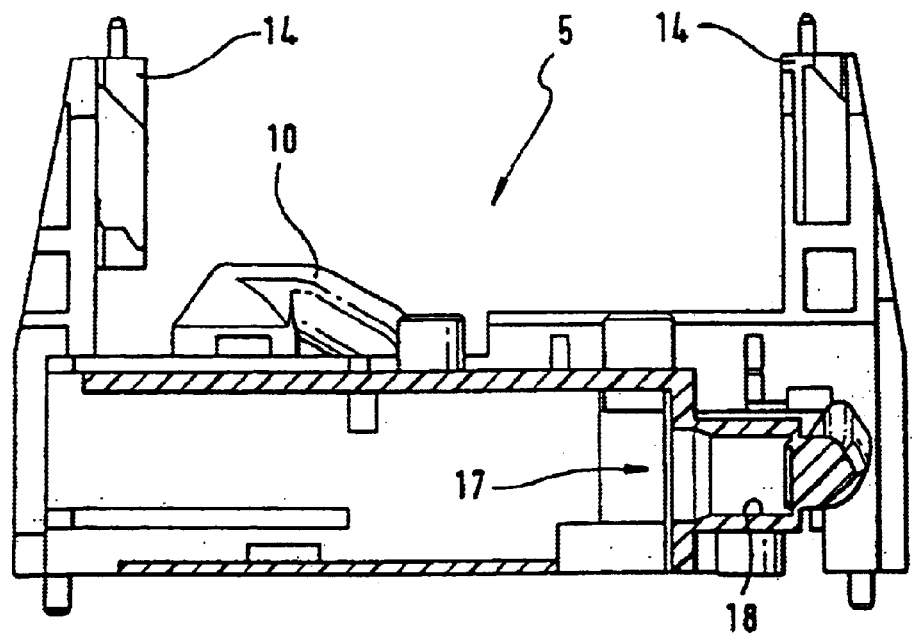
FIG. 9 is a sectional view of the parts mounting module taken along the line II—II of FIG. 5.

To effect a pressure tight coupling of the cuff 1, the pump 7 and the valve 8 to the fluid channels 10 formed in the parts mounting module 5, accuracy in the geometry of the sealing areas is necessary. As FIG. 9 shows, the port 17 for connection of the pump 7 has a cylindrical section 18. If applicable, a corresponding sealing element, particularly an O-ring, may be inserted between the corresponding connector necks of the pump 7 and the port 17.

Figure 10:
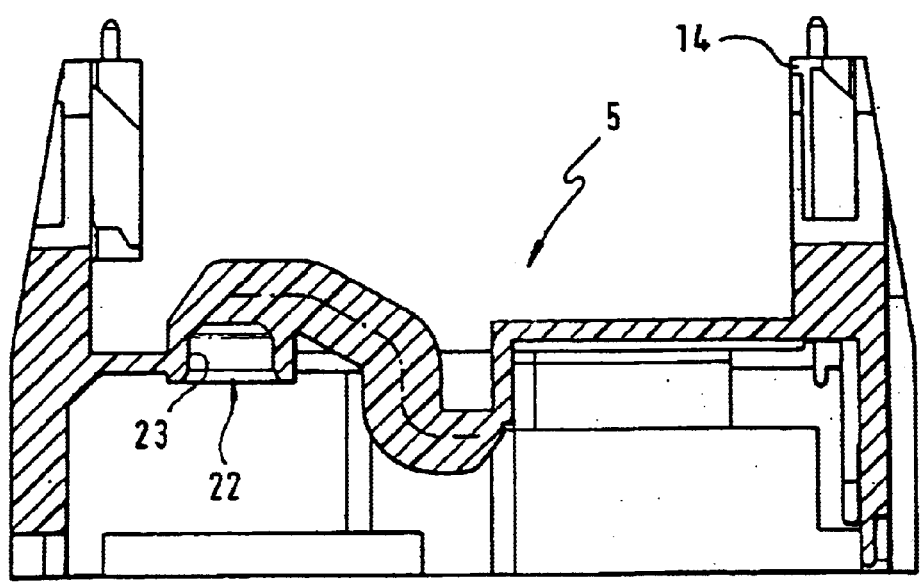
FIG. 10 is a sectional view of the parts mounting module taken along the line III—III of FIG. 5.

The port 22 for connection of the valve 8 is equally provided with a cylindrical section 23, as shown in FIG. 10. To enhance the sealing effect, it is likewise possible to insert an O-ring. In contrast to conventional blood pressure monitoring devices using tubing, the direct connection of the components of the fluid pressure system 6 with the fluid channels 10 integrally formed in the parts mounting module 5 affords the advantage of eliminating leakage at the tube neck which, under circumstances, would not be noticed until after a prolonged period of use. In particular, leakage resulting from aging and relative displacement due to pump vibrations or user handling is eliminated. A further obvious advantage is that the assembly of the components of the blood pressure monitoring device on the parts mounting module is extremely simplified lending itself to automation, because each component has its assigned bay on the mounting module and the components of the fluid pressure system are connected to a rigid fluid channel and not to a flexible fluid channel.

Owing to the special configuration of the parts mounting module particular advantages are achievable with the blood pressure monitoring device. In particular, by virtue of the special configuration of the fluid channels 10 the mounting module 5 may be adapted to the ergonomics of the wrist joint, hence enabling a good fit to be combined with a compact design. Furthermore, the central mounting module 5 reduces the cost of assembly considerably, because the individual components need only be inserted in the corresponding recesses and connector necks or points of attachment. To provide a seal between the connector necks and the components of the fluid pressure system 6 it is sufficient to use an O-ring, for example. With the described arrangement of the components the need to provide electrical wiring is obviated, all electrically powered parts being in direct electrical contact with the board by soldering.

With the parts mounting module 5 it is furthermore possible to provide for noise insulation of noise generating components as, for example, the pump 7, by means of suitable mounting module walls. The individual components may also be embedded in the mounting module so that the blood pressure monitoring device is not damaged when dropped onto the floor. The walls may be slightly yielding in such an event. If the individual components of the blood pressure monitoring device were installed or attached directly to the housing, they would be exposed to the shock on dropping more severely and more directly. Finally, the special configuration of the parts mounting module 5 permits enormous design freedom for the outer housing. Here the mounting module is configured as a chassis located in the interior of and separate from the housing. It will be understood, of course, that in one variant the fluid channels may also be provided in the housing itself. In this event the provision of a parts mounting module is not an absolute requirement.

What is claimed is:

1. A blood pressure monitoring device comprising:
a cuff;
a fluid pressure system for filling the cuff with fluid under pressure; and
a parts mounting module for components of the fluid pressure system, said parts mounting module made of a material and including a fluid channel integrated therein and serving to connect the components of the fluid pressure system, said fluid channel having a bounding wall that is completely formed by the material of the parts mounting module.

2. The blood pressure monitoring device according to claim 1 wherein the fluid channel is routed in a three-dimensional curvature extending in several planes.

3. The blood pressure monitoring device according to claim 2 wherein the path of the fluid channel extends in a manner free from sharp-edged kinks.

4. The blood pressure monitoring device according to claim 1 wherein the bounding wall is of an essentially uniform thickness.

5. The blood pressure monitoring device according to claim 1 wherein the parts mounting module is injection molded from plastics material and the fluid channel is formed by injecting gas into the plastics material of the parts mounting module prior to its complete cooling.

6. The blood pressure monitoring device according to claim 1 wherein the fluid channel branches into several fluid channels in the interior of the material of the parts mounting module.

7. The blood pressure monitoring device according to claim 1 wherein the fluid channel has ports into which corresponding components of the fluid pressure system are snap-fitted with an essentially complementary connector element.

8. A blood pressure monitoring device comprising:
a cuff;
a fluid pressure system for filling the cuff with fluid under pressure;
a parts mounting module for components of the fluid pressure system, said parts mounting module made of a material and including a fluid channel integrated therein and serving to connect the components of the fluid pressure system, said fluid channel having a bounding wall that is completely formed by the material of the parts mounting module, wherein all of the components of the fluid pressure system are mounted on the parts mounting module in bays specifically provided for each component; and
a housing enclosing the parts mounting module and the components of the fluid pressure system.

9. The blood pressure monitoring device according to claim 8 wherein the cuff is arranged on an underside, and wherein the components of the fluid pressure system include a pump, a pressure valve, and a pressure sensor, all of which are arranged on an upper side of the parts mounting module and are coupled to fluid channel ports.

10. The blood pressure monitoring device according to claim 9 wherein the pump, the pressure valve, and the pressure sensor each have an electrical connector, and wherein the electrical connectors of the pump, the pressure valve, and the pressure sensor are arranged to lie essentially in one plane.

11. The blood pressure monitoring device according to claim 9 wherein the parts mounting module includes a printed circuit board and the pump, the pressure valve, and the pressure sensor are connected directly to said printed circuit board.

12. The blood pressure monitoring device according to claim 1 wherein the fluid pressure system includes a pump, a pressure valve, a pressure sensor, and power supply contacts, each of the pump, the pressure valve, and the pressure sensor including an electrical connector; and the blood pressure monitoring device further comprises a printed circuit board carrying an electrical control unit for controlling the pump, the pressure valve and the pressure sensor, wherein the pump, the pressure valve, and the pressure sensor are arranged such that the electrical connections thereof are directly connected with the printed circuit board.

13. The blood pressure monitoring device according to claim 12, wherein the electrical connectors of the pump, the pressure valve, and the pressure sensor along with the power supply contacts lie essentially in one plane.

14. The blood pressure monitoring device according to claim 12, further comprising a parts mounting module receiving the pump, the pressure valve, and the pressure sensor, said parts mounting module made of a material and including a fluid channel integrated therein, said fluid channel having a bounding wall that is completely formed by the material of the parts mounting module.

15. The blood pressure monitoring device according to claim 1 further comprising:

a housing, wherein the cuff is adjacent to the housing; and the fluid pressure system comprises a pump, a pressure valve, and a pressure sensor, which are arranged in an interior of said housing; and a display device for indicating measured values, said display device being disposed on the housing;

wherein the parts mounting module is arranged in the interior of the housing and includes bays each of which is configured in particular to receive and in each of which is fastened a corresponding one of the pump, the pressure valve, and the pressure sensor.

16. The blood pressure monitoring device according claim 15, wherein each of the bays has a contour adapted essentially to the contour of the corresponding one of pump, the pressure valve, and the pressure sensor which it receives.

17. The blood pressure monitoring device according to claim 13, wherein the electrical connectors of the pump, the pressure valve, and the pressure sensor along with the power supply contacts lie essentially in a plane in which the printed circuit board is disposed for soldering to the electrical contacts.

18. A blood pressure monitoring device for use with a cuff, said device comprising:

a fluid pressure system for filling the cuff with fluid under pressure and for measuring the blood pressure, said fluid pressure system including a pump, a pressure valve, a pressure sensor, and power supply contacts, each of the pump, the pressure valve, and the pressure sensor including an electrical connector;

a printed circuit board carrying an electrical control unit for controlling the pump, the pressure valve and the pressure sensor, wherein the pump, the pressure valve, and the pressure sensor are arranged such that the electrical connections thereof are directly connected with the printed circuit board; and a parts mounting module receiving the pump, the pressure valve, and the pressure sensor, the parts mounting module made of a material and including a fluid channel integrated therein, the fluid channel having a bounding wall that is completely formed by the material of the parts mounting module.

19. The blood pressure monitoring device according to claim 18 wherein the fluid channel is routed in a three-dimensional curvature extending in several planes.

20. The blood pressure monitoring device according to claim 19 wherein the path of the fluid channel extends in a manner free from sharp-edged kinks.

21. The blood pressure monitoring device according to claim 18 wherein the bounding wall is of an essentially uniform thickness.

22. The blood pressure monitoring device according to claim 18 wherein the parts mounting module is injection molded from plastics material and the fluid channel is formed by injecting gas into the plastics material of the parts mounting module prior to its complete cooling.

23. The blood pressure monitoring device according to claim 18 wherein the fluid channel branches into several fluid channels in the interior of the material of the parts mounting module.

24. The blood pressure monitoring device according to claim 18 wherein the fluid channel has ports into which corresponding components of the fluid pressure system are snap-fitted with an essentially complementary connector element.

* * * * *